(12) United States Patent
Oraevsky et al.

(10) Patent No.: US 9,545,456 B2
(45) Date of Patent: Jan. 17, 2017

(54) OPTOACOUSTIC-ULTRASONIC CONTRAST AGENTS WITH ENHANCED EFFICIENCY

(71) Applicants: Alexander A Oraevsky, Houston, TX (US); Anton Liopo, Houston, TX (US); Sergey A Ermilov, Houston, TX (US)

(72) Inventors: Alexander A Oraevsky, Houston, TX (US); Anton Liopo, Houston, TX (US); Sergey A Ermilov, Houston, TX (US)

(73) Assignee: TomoWave Laboratories, Inc., Houston, TX (US)

( * ) Notice: Subject to any disclaimer, the term of this patent is extended or adjusted under 35 U.S.C. 154(b) by 5 days.

(21) Appl. No.: 13/774,876

(22) Filed: Feb. 22, 2013

(65) Prior Publication Data

US 2014/0066761 A1 Mar. 6, 2014

Related U.S. Application Data

(60) Provisional application No. 61/601,744, filed on Feb. 22, 2012.

(51) Int. Cl.
  *A61B 5/00* (2006.01)
  *A61K 49/22* (2006.01)
  *A61B 8/08* (2006.01)

(52) U.S. Cl.
  CPC .......... *A61K 49/223* (2013.01); *A61B 5/0035* (2013.01); *A61B 5/0095* (2013.01); *A61B 8/481* (2013.01); *A61B 8/5261* (2013.01)

(58) Field of Classification Search
  CPC .............. B22F 1/0018; B22F 1/0044; A61K 47/48861; A61K 47/48869; A61K 47/48876; A61K 47/482; B82Y 40/00
  USPC .......... 600/437–480; 424/9.323, 1.65, 1.11; 427/127; 75/255, 348, 351, 362
  See application file for complete search history.

(56) References Cited

U.S. PATENT DOCUMENTS

| | | | |
|---|---|---|---|
| 7,029,514 B1* | 4/2006 | Yang et al. | 75/348 |
| 2006/0070491 A1* | 4/2006 | Yang et al. | 75/255 |
| 2009/0324494 A1* | 12/2009 | Ham et al. | 424/1.65 |
| 2011/0104077 A1* | 5/2011 | Hua et al. | 424/9.323 |
| 2013/0045160 A1* | 2/2013 | Ham et al. | 424/1.11 |
| 2013/0344237 A1* | 12/2013 | Guo | 427/127 |

\* cited by examiner

*Primary Examiner* — Sanjay Cattungal
(74) *Attorney, Agent, or Firm* — Benjamin Aaron Adler (57) ABSTRACT

Provided herein are dual contrast agents or nanocomposite particles designed to enhance optoacoustic-ultrasonic imaging. The contrast agents or particles have a core designed to enhance response to incident transient ultrasonic pressure waves and at least two layers disposed around the core. The inner first layer is designed to effectively absorb incident transient optical waves, convert absorbed optical energy into heat and demonstrates significant thermal expansion and/or conversion of thermal energy into acoustic pressure. The outer second layer thermally insulates the inner layer from the surrounding aqueous environment and enhances the generation of transient ultrasonic pressure waves during optoacoustic-ultrasonic imaging and sensing. Also provided are methods of enhancing contrast in a tissue optoacoustic-ultrasonic imaging and producing enhanced optoacoustic images by contacting the tissue with the dual contrast agent or nanocomposite particles.

24 Claims, 9 Drawing Sheets

OPTOACOUSTIC-ULTRASONIC CONTRAST AGENTS WITH ENHANCED EFFICIENCY

CROSS-REFERENCE TO RELATED APPLICATION

This non-provisional application claims benefit of priority under 35 U.S.C. §119(e) of provisional application U.S. Ser. No. 61/601,744, filed Feb. 22, 2012, now abandoned, the entirety of which is hereby incorporated by reference.

BACKGROUND OF THE INVENTION

Field of the Invention

The present invention generally relates to the fields of optoacoustic-ultrasonic methods and contrast agents suitable for imaging and sensing purposes, and in particular, but not limited to, nanocomposite particles designed to have properties to maximize contrast during optoacoustic-ultrasonic imaging and sensing procedures.

Description of the Related Art

Optoacoustic imaging, sensing and monitoring are rapidly emerging biomedical technologies with significant potential for a growing number of applications in detection and treatment of cancer and vascular diseases (1). Combining optoacoustic imaging with ultrasonic imaging is technologically natural and beneficial from a biomedical prospective because the two types of imaging provide complementary information to the physician (2). The acoustic contrast of ultrasonic imaging based on density and speed of sound can provide fine morphological details, while optoacoustic imaging has better contrast for blood and can be used to acquire functional information with molecular specificity. That is why optoacoustic molecular and functional imaging combined and coregistered with ultrasonic imaging is thought to have the most merit for health care.

Exogenous contrast agents are administered to the body for purposes of biomedical imaging, sensing and monitoring therapeutic and surgical interventions in situations where a specific volume in the body of medical interest does not have sufficient endogenous contrast. While ultrasonic contrast agents based on encapsulated gas bubbles have been developed and used in clinics, necessarily nontoxic and sufficiently effective optoacoustic contrast agents have not been developed. Ultrasonic contrast agents are relatively successful because biological tissues do not possess strong echogenicity. The problem and the challenge associated with optoacoustic imaging is that optoacoustic contrast agents must effectively compete with the contrast of red blood cells and achieve sufficient contrast enhancement in concentrations substantially lower than the concentration of hemoglobin in blood.

With a large number of proposed designs for optoacoustic contrast agents (3) and recently two different designs for dual modality optoacoustic-ultrasonic contrast agents (4-6), none of them met the challenge of being necessarily non-toxic and sufficiently effective in generation of ultrasonic, i.e., pressure, waves in response to optical illumination. Contrast agents based on nanocomposite particles are more effective compared with molecular probes because the optoacoustic signals they emit or ultrasonic signals they reflect are proportional to their volume.

Thus, there is a present need for dual contrast agents with improved capabilities for contrast enhanced optoacoustic-ultrasonic imaging and sensing in vivo or in vitro. Specifically, the prior art is deficient in non-toxic, nanocomposite particles that both generate and reflect detectable ultrasonic signals upon interaction with optical and ultrasonic energy. The present invention fulfills this longstanding need and desire in the art.

SUMMARY OF THE INVENTION

The present invention is directed to a dual contrast agent designed to enhance optoacoustic-ultrasonic imaging. The dual contrast agent comprises a nanocomposite particle that a core effective to enhance response to incident transient ultrasonic pressure waves and at least two layers disposed around the core. The two layers may be a first inner layer comprising at least one compound effective to absorb incident transient optical energy, convert absorbed optical energy into heat, where the compound significantly thermally expands or converts thermal energy into acoustic pressure or both and a second thermally insulating outer layer comprising at least one compound effective to insulate the inner layer from a surrounding aqueous environment, wherein the design of the nanocomposite particle enhances generation of transient ultrasonic pressure waves during optoacoustic-ultrasonic imaging. The present invention is directed to a related nanocomposite particle that comprises at least two layers where the contrast agent further comprises a thin bonding layer disposed between the adjacent layers.

The present invention also is directed to method for enhancing contrast in a tissue volume of interest in a subject during optoacoustic-ultrasonic imaging. The method comprises the steps of contacting the tissue volume of interest with the dual contrast agent described herein, delivering incident optical energy to the tissue volume of interest and to the dual contrast agent and delivering ultrasonic energy to the tissue volume of interest and to the dual contrast agent. The nanocomposite particle comprising the dual contrast agent generates and emits detectable ultrasonic pressure waves upon interaction with the incident optical energy in addition to ultrasonic pressure waves generated and emitted by the tissue volume and reflects the incident ultrasonic energy upon interaction therewith in addition to incident ultrasonic energy reflected by the tissue volume. The addition of the detectable ultrasonic pressure waves and reflected ultrasonic energy from the dual contrast agent thereby enhances contrast in the tissue volume during optoacoustic-ultrasonic imaging.

The present invention is directed further to a nanocomposite particle. The particle comprises a core and first, second and third layers adjacently disposed around the core. The core comprises a fluid having ultrasound generating properties at a predetermined range of electromagnetic wavelengths. The first layer is disposed around the core and comprises one or more optical energy absorbing compounds effective to convert absorbed optical energy into heat and thermally expand. A a second layer is disposed around the first layer and comprises a thermally insulating compound with an acoustic impedance lower than the first layer or matching that of biological tissue or a combination thereof. The third layer is disposed around the second layer and comprises a nanocomposite particle bioprotective compound or a targeting vector or a combination thereof. The present invention is directed to a related nanocomposite particle further comprising a bonding layer or linker disposed between adjacent layers.

The present invention is directed further still to an optoacoustic-ultrasound imaging method with enhanced contrast. The method comprises the steps of targeting a plurality of the nanocomposite particles of described herein to the tissue volume of interest in a subject and delivering optical energy and ultrasound energy to the tissue volume and nanocomposite particles. detecting The ultrasonic pressure waves generated by the tissue and by the nanocomposite particles upon interaction with the optical energy are detected. The ultrasonic energy reflected by the tissue and by the nanocomposite particles upon interaction therewith are also detected. An optoacoustic-ultrasound image is produced based on a combination of the detected ultrasonic pressure waves and on a combination of the reflected ultrasonic energy from the tissue and nanocomposite particle, where the combination provides an image with enhanced contrast.

Other and further aspects, features, and advantages of the present invention will be apparent from the following description of the presently preferred embodiments of the invention given for the purpose of disclosure.

BRIEF DESCRIPTIONS OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "optoacoustic contrast agent" refers to a medium that absorbs electromagnetic energy and converts it into acoustic pressure waves, which propagate as ultrasound. The most useful range of electromagnetic energy is the near-infrared spectral range from about 650 nm to about 1250 nm.

As used herein, the term "ultrasonic contrast agent" refers to a medium that that can scatter, i.e., reflect or deflect, ultrasonic waves in the frequency band ranging in different applications from about 1 MHz to about 100 MHz.

As used herein, the term "nanocomposite particle" refers to a particle having parts or layers having dimensions measured in nanometers, i.e. less than a micron. Necessary and sufficient conditions for the design of particles employed in contrast enhanced biomedical optoacoustic-ultrasonic imaging and sensing are met. As such, the nanocomposite particles can generate ultrasonic, i.e., pressure, signals that are detectable when these particles are present in blood in concentrations nontoxic to animals or humans. To satisfy these conditions, the particle is designed such that its ability to emit pressure wave in response to optical illumination and to reflect a pressure wave of incoming ultrasound is maximized. Thus, the nanocomposite particles comprise an optoacoustic-ultrasonic contrast agent. Use of the terms "nanocomposite particle" and "particle" are interchangeable.

As used herein, the term "subject" refers to a human or other mammal or animal or to any portion or body part thereof to which a contrast agent, dual contrast agent or nanocomposite particle, as described herein, may be delivered for contrast enhanced biomedical optoacoustic-ultrasonic imaging and sensing.

In one embodiment of the present invention there is provided a dual contrast agent designed to enhance optoacoustic-ultrasonic imaging, comprising a nanocomposite particle having a core effective to enhance response to incident transient ultrasonic pressure waves and at least two layers disposed around the core, the two layers comprising a first inner layer comprising at least one compound effective to absorb incident transient optical energy, convert absorbed optical energy into heat, wherein said compound significantly thermally expands or converts thermal energy into acoustic pressure or both; and a second thermally insulating outer layer comprising at least one compound effective to insulate the inner layer from a surrounding aqueous environment, wherein the design of the nanocomposite particle enhances generation of transient ultrasonic pressure waves during optoacoustic-ultrasonic imaging.

Further to this embodiment the nanocomposite particle may comprise at least two layers, the contrast agent further comprising a thin bonding layer disposed between said adjacent layers. In this further embodiment the bonding layer may comprise a linking molecule, a linking substance or a linking medium.

In both embodiments the core may comprise a gas, liquid or emulsion having ultrasound generating properties upon interaction with incident optical energy and ultrasound reflecting properties upon interaction with incident ultrasound energy. Particularly, the gas is air, a perfluorocarbon gas or nitrogen or other heavy gas. Alternatively, the liquid or emulsion is expandable upon heating or convertible to a gas.

Also in both embodiments the nanocomposite particle may comprise up to five adjacent layers surrounding the core, the core comprising a heavy gas or a liquid having a low energy threshold for transition into gas that can reflect and deflect ultrasonic waves; a first layer comprising an expandable and contractible polymer, protein, lipid or polysacharide disposed in a mechanically confining relationship to the core; a second layer of an optoacoustically active medium comprising a matrix of biodegradable substances having a significant thermal expansion coefficient and strong thermo-acoustic efficiency, said matrix comprising one or more of inclusions or embedded molecules nanoparticles with a strong optical absorption peak in at least one predetermined wavelength or wavelength range, the inclusions effective to rapidly and effectively nonradiatively convert optical energy into heating of the matrix; a third thin bonding layer comprising one or more silica compounds as an adhesive between adjacent layers; a fourth thermally insulating layer comprising one or more compounds wherein the fourth layer has an acoustic impedance lower than the second optoacoustically active layer; a fifth biocompatibility and biomolecular targeting layer comprising a biocompatible polyethylene-glycol (PEG) and one or more targeting agents or vectors. In this embodiment each of the layers may comprise separately or in combination smaller layer portions, sublayers or subcomponents.

Particularly in all embodiments the first layer compound comprises one or more of a metal having plasmonic resonance at a predetermined range of wavelengths, a polymer, a protein, a sugar, or a lipid each with embedded or intercalated absorbing molecules or small nanoparticles. Representative example of the metal are gold, silver or platinum, representative examples of the polymer are poly(lactic-co-glycolic acid) (PLGA), representative examples of the protein is albumin, and representative examples of the sugar is chitosan or galactose. Also, the second layer compound may be an ultra-high-molecular-weight polyethylene, polyvinylidene fluoride, polytetrafluoroethylene, high impact polystyrene, or nylon-6. In addition the third layer silica compound may be tetraethyl orthosilicate, 3-aminopropyltriethoxysilane, 3-(trimethoxysilyl)propyl methacrylate, ethyl silicate, sodium silicate or other bonding liquids. Furthermore, the one or more compounds comprising the fourth layer are porous silica, silicon dioxide, or polyacrylic acid (PAA). Further still the targeting agent or vector may antibodies or active fragments thereof, RGD peptides or other peptides, aptamers, folic acid, or viruses.

In another embodiment of the present invention there is provided a method for enhancing contrast in a tissue volume of interest in a subject during optoacoustic-ultrasonic imaging, comprising the steps of contacting the tissue volume of interest with the dual contrast agent as described supra; delivering incident optical energy to the tissue volume of interest and to the dual contrast agent; and delivering ultrasonic energy to the tissue volume of interest and to the dual contrast agent; where the nanocomposite particle comprising the dual contrast agent generates and emits detectable ultrasonic pressure waves upon interaction with the incident optical energy in addition to ultrasonic pressure waves generated and emitted by the tissue volume and reflects the incident ultrasonic energy upon interaction therewith in addition to incident ultrasonic energy reflected by the tissue volume, where addition of the detectable ultrasonic pressure waves and reflected ultrasonic energy from the dual contrast agent thereby enhancing contrast in the tissue volume during optoacoustic-ultrasonic imaging.

In yet another embodiment of the present invention there is provided a nanocomposite particle, comprising a core comprising a fluid having ultrasound generating properties at a predetermined range of electromagnetic wavelengths; a first layer disposed around the core comprising one or more optical energy absorbing compounds effective to convert absorbed optical energy into heat and thermally expand; a second layer disposed around the first layer comprising a thermally insulating compound with an acoustic impedance lower than the first layer or matching that of biological tissue or a combination thereof; and a third layer disposed around the second layer comprising a nanocomposite particle bioprotective compound or a targeting vector or a combination thereof. Further to this embodiment the nanocomposite particle may comprise the bonding layer or linker, as described supra.

In both embodiments the core fluid is air, perfluorocarbon gas or nitrogen or other heavy gas or is a liquid or emulsion that is expandable upon heating or convertible to a gas. Also, each of the layers may comprise separately or in combination smaller layer portions, sublayers or subcomponents. In addition the first layer compound may comprise one or more of a metal having plasmonic resonance at a predetermined range of wavelengths, a polymer, a protein, a sugar, or a lipid each with embedded or intercalated absorbing molecules or small nanoparticles. Representative examples of the metal, polymer, protein and sugar are as described supra. Furthermore, the second layer compound may be silica oxide or a polymer. Further still, the third layer polymer is polyethylene glycol (PEG) and the targeting vector is one or more of a peptide, an antibody, an aptamer, a nucleotide, or a virus.

In yet another embodiment of the present invention there is provided an optoacoustic-ultrasound imaging method with enhanced contrast, comprising the steps of targeting a plurality of the nanocomposite particles, as described supra, to the tissue volume of interest in a subject; delivering optical energy and ultrasound energy to the tissue volume and nanocomposite particles; detecting ultrasonic pressure waves generated by the tissue and by the nanocomposite particles upon interaction with the optical energy; detecting ultrasonic energy reflected by the tissue and by the nanocomposite particles upon interaction therewith; and producing an optoacoustic-ultrasound image based on a combination of the detected ultrasonic pressure waves and on a combination of the reflected ultrasonic energy from the tissue and nanocomposite particle, wherein the combination provides an image with enhanced contrast.

Provided herein are nanocomposite particles as contrast agents for optoacoustic-ultrasonic imaging and either optical or ultrasonic treatment. These particles possess optical, acoustic, thermal, mechanical and biochemical properties that make them effective contrast agents when they interact with light and/or ultrasound. This nanocomposite comprises materials, each of which has its own properties that enhance efficiency of these particles as contrast media. The composition and structure of these particles is layered, and each next or adjacent layer is designed or constructed to enhance properties of the previous layer.

The compounds and materials comprising the nanocomposite particles have a strong optical absorption cross-section such that these particles effectively absorb near-infrared light at specific desirable wavelength or simultaneously a number of wavelengths. Generally, the compounds and materials comprising the nanocomposite particles also may effectively convert incident or absorbed optical energy into heat and a substantial thermal expansion and, as such, effectively generate waves of thermal pressure, i.e., pressure waves, which propagate as ultrasound. The nanocomposite particles may be further coated with thermally insulating and acoustically rigid materials. The compounds and materials comprising the nanocomposite particles may have an acoustic impedance significantly different from that of water or biological tissues and, as such, may effectively reflect ultrasound. The compounds and materials comprising the outer most layer of the nanocomposite particles may have biochemical properties that enable the particles to circulate in the blood of live human or animal subjects for a long time while accumulating in the target tissue volume of medical interest. Such nanocomposite particle design enables the particles to serve as a dual, i.e., optoacoustic and ultrasonic, contrast agent.

Provided herein are nanocomposite particles and the designs of particles that can serve as a superior dual, i.e., optoacoustic and ultrasonic, contrast agent, the design thereof and methods of their use. The nanocomposite particles have either a spherical shape or an elongated shape, such as paraboloid. The nanocomposite particles have a layered composition comprising an inner core around which layers typically made through a layer by layer assembly.

The inner core of the particle is either a heavy gas or liquid. Gas is preferred for enhancement of ultrasonic contrast efficiency, or, alternatively, if a liquid is used, the liquid that has relatively low thermal energy threshold required for phase transition into gas, such as, but not limited to, liquid perfluorocarbon. An optically absorbing liquid is preferred for enhancement of optoacoustic contrast efficiency. Preferably absorption is in the near-infrared optical spectrum of electromagnetic radiation. If the liquid is not absorbing, it can be used to dissolve absorbing molecules, ions or other substances or nanoparticles having strong near-infrared absorption. The liquid, if not easily transformed into gas, preferably has a large thermal expansion coefficient.

The nanocomposite particles have multiple layers of materials, preferably 5 layers, with properties selected to serve specific purposes essential for efficiency of optoacoustic and ultrasonic contrast. In some designs properties and corresponding purposes of two or more layers can be combined in one composite layer. While the particle core is designed primarily for purposes of ultrasonic contrast, one of the layers is designed specifically as a source of optoacoustic contrast. The optoacoustically active layer can be made of various materials, for example metals with plasmon resonance properties, organic- and bio-polymers, polysaccharides, lipid blocks, proteins and other biodegradable matrix substances.

All selected materials should result in (i) a strong optical absorption in the desirable range of electromagnetic wavelengths, (ii) the ability to convert absorbed optical energy into heat and (iii) a high thermo-acoustic efficiency (Gruneisen parameter). If the matrix of the optoacoustic active layer does not possess strong optical absorption, the optical absorption can be increased by using strongly absorbing molecules or particles intercalated or otherwise embedded within the matrix.

A critically important layer of the nanocomposite particle is the thermally insulating layer disposed around the optoacoustically active layer. This layer inhibits conductance and diffusion of thermal energy from the optoacoustic layer to surrounding aqueous medium during the optical, i.e., electromagnetic, energy deposition into the particle, thereby significantly enhancing optoacoustic efficiency. For increased efficiency of launching ultrasonic waves from the particle into the surrounding medium, the acoustic impedance of each next outer layer is either matched or lower than each previous inner layer. The final outmost layer is biological for biocompatibility with live tissues, such as the immune system of blood, and optionally, purposes of selective targeting of specific molecular receptors in the volume of medical interest.

In biomedical applications of imaging sensing and monitoring sometimes it is preferred that contrast agent particles have specific dimensions in order to be the most effective and/or nontoxic. Depending on a design for a specific application, the particle may have a size from about 10 nanometers to about 10 micrometers. With increased dimensions capability of the particle to emit strong optoacoustic or ultrasonic signals is increased, however, toxicity also may be increased and the ability to target specific cellular receptors or volumes of medical interest in the body can be decreased. For specific biomedical application, the nanoparticles and/or microparticles may be injected into blood, interstitially, applied topically, applied locally, subcutaneously, and/or orally depending on application and particle size, shape, and/or material. The nanoparticles and/or microparticles may be delivered using passive delivery or active delivery with targeting agents.

Preferably, the contrast agent particle is made of smaller particles or molecules with dimensions from about 1 nanometer to about 1 micrometer, so that it can be easier extracted (expelled) from the body while biodegrading after fulfilling its contrast agent purposes. In designing nanocomposite particles it must be considered that decrease of the particle size reduces ultrasonic efficiency faster than it reduces optoacoustic efficiency. A particle can absorb optical energy even from an electromagnetic wave with a wavelength much longer than the dimensions of the particle, while a particle cannot effectively interact, i.e., scatter, ultrasonic energy incident with a wavelength much longer than the particle characteristic dimensions.

The nanocomposite particles of this invention possesses properties that enable maximum contrast during optoacoustic-ultrasound imaging or sensing processes. The particles have a strong optical absorption in the wavelength range useful for biomedical imaging, sensing and monitoring. The most useful range is the near-infrared from about 650 nm to about 1250 nm. The particles rapidly convert of the absorbed optical energy into heat, have a strong thermal expansion and/or large value of thermo-acoustic efficiency, and comprise thermal insulation on the outside of optoacoustically active layer, thereby effectively generating pressure in response to rapid optical heating. The particles have a high acoustic impedance mismatch of the particle core and water or water-containing biological tissues, so that acoustic, i.e., pressure, waves can reflect and refract from the contrast agent very effectively within a wide range of ultrasonic frequencies. The range from about 1 MHz to about 100 MHz is the widest practically useful range. The particles have the ability to generate strong ultrasonic signals in response to either optical illumination or ultrasonic excitation, thus serving as a multi-functional optoacoustic-ultrasonic contrast agent. The particles have the ability to perform biological functions such as protection from the immune system, capability to circulate in the blood for a longer period of time, and capability to target cellular receptors and other cellular targets through high affinity of a targeting agent (peptide, monoclonal antibody, aptamer, etc) conjugated to the surface of said particle.

The nanocomposite particles, may comprise, for example, but not limited to nanoparticles and/or microparticles surrounded by a polymer matrix shell. The polymers can either be surface erodible polymers such as polyanhydrides or bulk erodible polymers such as poly-ortho-esters or combinations or mixtures thereof. Preferably, the polymers are biocompatible, biodegradable polymers. Examples of preferred polymers are biodegradable copolymers such as lactic acid and glycolic acid copolymers and combinations or mixtures thereof which are among the synthetic polymers approved for human clinical use. They are biocompatible and their degradation products are low molecular weight compounds, such as lactic acid and glycolic acid, which enter into normal metabolic pathways. Furthermore, copolymers of poly(lactic-co-glycolic acid) offer the advantage of a large spectrum of degradation rates from a few days to years by simply varying the copolymer ratio of lactic acid to glycolic acid. PLA (poly lactic acid) and PLGA (copoly lactic acid/glycolic acid) are superior in biocompatibility and biodegradability, and are useful materials as base material for sustained-release formulation.

To enhance bio-degradation of the polymers used in biological application, the nanocomposite particles can also include enzymes that can facilitate the biodegradation of the polymers used in the composition. The interaction of the nanoparticles or microparticles with electromagnetic radiation or acoustic (ultrasonic) waves can include heating of the particles and surrounding medium (tissue) that, in turn, can result in acoustic wave formation, acoustic wave absorption or reflection (refraction) depending on parameters of electromagnetic irradiation and/ultrasound wave ultrasonification.

The surface of the polymer shell is prepared for functionalization by providing carboxyl groups and/or amine groups or thiol or other groups useful for conjugation of biological molecules. The functionalization is completed by providing polyethylene-glycol (PEG) of two types, one is "short" for further conjugation with targeting vectors and one is "long" for protection of this particle against immune system, for example, of blood, of living organisms. It is significant that the length of conjugated molecules is optimized. The best functional performance of the nanocomposite particle can be achieved only when the length of the "long" PEG chain is equal or about equal the total length of the "short" PEG chain plus the length of conjugated targeting vector or agent, such as antibody or peptide, if present. More preferably, the length of the long PEG is very slightly longer than that of the targeting vector molecule.

Nanoparticles and/or microparticles suitable for use in this invention may include, without limitation, metal particles, semiconductor particles, dielectric particles, metal-coated dielectric particles, metal coated semiconductor particles, polymer particles, metal coated polymer particles, bio-compatible polymer particles, bio-degradable polymer particles, or mixtures and combinations thereof.

Nanoparticles and/or microparticles comprising the nanocomposite particles may include solid, liquid, gas particles, or mixtures or combinations thereof. Liquid nanoparticles and/or microparticles are in the form of droplets. The gaseous core of the nanoparticles and/or microparticles are in the form of nano-bubbles and/or micro-bubbles. In one example the nanoparticles may be made of gold, silver, platinum, carbon or mixtures and combinations thereof. In another example, the nanoparticles may be nano-shelled particles having a core of one material and a shell of another material. The nanoparticles include, but not limited to, spheres, rods, cylinders, disks, shells, tubes, including nanotubes, irregular-shaped particles or mixtures and combinations thereof.

Conjugates of porphyrin, chlorophyll and bacteriochlorophyll absorbers with RGD-containing peptides or RGD peptidomimetics are useful for optoacoustic imaging and for laser thermal therapy of tumors and vascular diseases, such as age-related macular degeneration, and for diagnosis of tumors by optoacoustic imaging methods. Particularly, the optically absorbing compounds for optoacoustic imaging comprise porphyrins and their derivatives, for example, where there is a central metal atom, other than magnesium, complexed to the four pyrrole rings, and/or the peripheral substituents of the pyrrole rings are modified and/or the macrocycle is dihydrogenated to chlorophyll derivatives (chlorins) or tetrahydrogenated to bacteriochlorophyll derivatives (bacteriochlorins). Due to their intense absorption in the near-infrared spectral region (650-850 nm) and their ready degradation after treatment, chlorophyll (Chl) and bacteriochlorophyll (BChl) derivatives are excellent optical absorbers for optoacoustics of tumors and have superior properties in comparison to porphyrins. Bacteriochlorophylls are of potential advantage compared to the chlorophylls because they show intense near-infrared bands, i.e., at considerably longer wavelengths than chlorophyll derivatives.

For biomedical applications, nanocomposite microparticles were used quantification of transit time through tissue and molecular imaging in tissues using ligands on the particle surface that bind to targets within vasculature. These particles can be also used for delivery of genes and drugs which can be released locally by disruption of the microbubbles with high-energy ultrasound or laser energy. Commercially available microbubbles can be used for conjugation with photosensitizers to yield a contrast agent for optoacoustic imaging and can be conjugated further with vectors (mAb, peptides or small molecular ligands) for specific targeting. However, microbubbles must be selected with diameters less than 5-6 microns. The limitation on size for clinical microbubbles use is determined by the diameter of the capillaries.

In an exemplary embodiment nanocomposite microspheres are synthesized by encapsulating small gold nanorods or a strongly absorbing and non-fluorescent near-infrared dye or porphyrins or rhodopsin inside a biodegradable polymer matrix shell.

In another exemplary embodiment nanocomposite particles comprise porphyrins encapsulated in a polymer matrix. These particles are stable in circulation.

In yet another exemplary embodiment a contrast agent comprises microbubbles with encapsulated gold nanorods (GNRs). The gas-filled microbubbles, whose diameters range from submicrometer to several micrometers, are not only echogenic but also can serve as drug-delivery vehicles. The gold nanorods are used to enhance the generation of both optoacoustic and photothermal signals. The optical absorption peak of the gold nanorods is tuned to any wavelength in the near-infrared spectral range and is invariant after microbubble encapsulation. This dual-modality contrast agent can also be used for laser thermotherapy. The optoacoustic imaging can be used to monitor temperature increases during the treatment. The targeting capability of GNRs was verified, and the temperature increased for a laser power of CW irradiation with laser power, demonstrates the potential of combined diagnosis and therapy with the dual-modality agent.

In yet another exemplary embodiment clinical application of hollow microparticles and nanoparticles. i.e. hollow spheres, may comprise phospholipids and liposomes, albumins or other proteins, or biopolymers, such as PLGA, PVA, Chitosan. As is known in the art liposomes are artificially-prepared vesicles primarily composed of a lipid bilayer. Liposomes can be prepared by disrupting biological membranes. Liposomes are composed of natural phospholipids, and may also contain mixed lipid chains with surfactant properties, liposome design may employ surface ligands for attaching to abnormal tissue/cells.

Gas-filled hollow spheres produce strong acoustic scattering relative to surrounding tissue. On the other hand, metallic nanoparticles, such as silver and gold, are usually applied to enhance optoacoustic signal intensity. They can be formed into different shapes. For example, gold nanorods (GNRs) can be tuned to match the desired peak absorption based on their aspect ratio, and their peak optical absorption wavelength is typically set to be in the near infrared spectral range for biomedical applications. Incorporation of both contrast agents ensures that GNRs and hollow spheres travel together and thus can be simultaneously detected. Carbon nanotubes and even carbon of India ink can be used as optical absorption contrast. Polymer-based microbubbles encapsulating india ink can generate OA-US signals efficiently but provide optical absorption without spectral selectivity.

In yet another exemplary embodiment a nanocomposite microparticle with gas core is designed not to be rapidly taken up by the immune system. Such particle uses hydrophobic materials, which increases the particle's residence time in the circulation and in turn, time available for contrast enhanced imaging. The particle is designed with significant mechanical elasticity so that to increase ultrasonic energy said particle can withstand before bursting. Preferred microparticles with a gas core are made of albumin, galactose, lipid, or biopolymers. The gas core is the most important part of the ultrasound contrast agent because it determines value of ultrasound scattering. Gas cores can comprise air or nitrogen or heavy gases such as perfluorocarbon. Heavy gases are less water-soluble so they are less likely to leak out from the microparticle, which can remain longer in circulation.

In yet another exemplary embodiment mixed liquid perfluorocarbon droplets with dimensions about 5 times smaller than red blood cells were encapsulated into a biopolymer particle and used as ultrasound contrast agent in the frequency range of 2 to 10 MHz.

In yet another exemplary embodiment, a particle is used for biomedical applications as a dual optoacoustic-ultrasonic contrast agent. The particle comprises albumin-shelled microbubble with dimensions ranging from 1 to 5 micrometers containing encapsulated hollow gold nanospheres. The gas-filled microbubble can effectively reflect wide-band ultrasound and also can serve as effective optoacoustic contrast agent. In addition, the hollow gold nanospheres are loaded with anticancer drugs. Under pulsed laser illumination at the wavelength in the peak of plasmon resonance absorption, the gold nanoshells effectively emit optoacoustic signals. The plasmon resonance of said hollow nanospheres is tuned to 805 nm and it does not change after microbubble encapsulation. When irradiated with continuous wave laser energy at the same wavelength the gold nanoshells release the load of drugs into cancer cells. Multi-modality contrast agent of this embodiment has a number of theranostic applications.

As described below, the invention provides a number of advantages and uses, however such advantages and uses are not limited by such description. Embodiments of the present invention are better illustrated with reference to the Figure(s), however, such reference is not meant to limit the present invention in any fashion. The embodiments and variations described in detail herein are to be interpreted by the appended claims and equivalents thereof.

Figure 1:
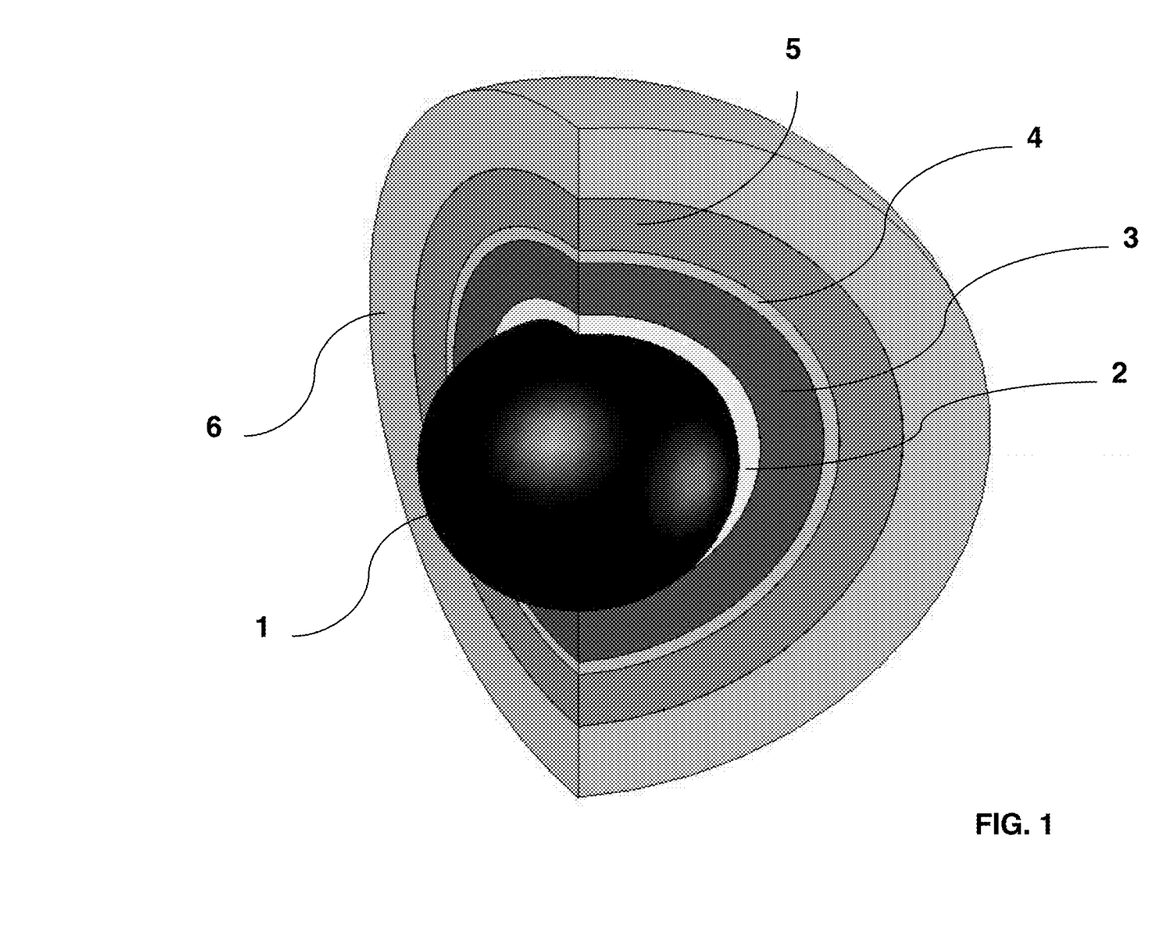
FIG. 1 depicts a nanocomposite particle assembly in cross-section.

FIG. 1 shows the design assembly of a nanocomposite particle that effectively generates acoustic pressure waves in response to pulsed optical illumination and simultaneously effectively scatters ultrasonic waves. The particle comprises a core 1 of a heavy gas or a liquid that has a low energy threshold for transition into a gas that can reflect/deflect ultrasonic waves. Around the core there is a first layer 2 is disposed. Layer 2 may comprise a polymer, a protein, a lipid or a polysacharide that mechanically confines the core. Layer 2 has the property of "breathing" i.e. expanding and contracting. Around layer 2, a second layer 3 is disposed. Layer 3 may comprise an optoacoustically acive medium comprising matrix biodegradable substances, such as, but not limited to, ultra-high-molecular-weight polyethylene, polyvinylidene fluoride, polytetrafluoroethylene, high impact polystyrene, nylon-6, etc., with a significant thermal expansion coefficient and a strong thermo-acoustic efficiency (Gruneisen parameter). The matrix contains small molecule absorbers, such as inclusions or embedded molecules and/or nanoparticles with strong optical absorption peak in predetermined at least one wavelength or wavelength range which have a rapid and an effective nonradiative conversion of optical energy into heating of the matrix. Around layer 3, a third layer 4 is disposed. Layer 4 is a thin bonding layer comprising one or more of tetraethyl orthosilicate; 3-Aminopropyl-triethoxysilane, 3-(trimethoxysilyl) propyl methacrylate, ethyl silicate, sodium silicate or other similar bonding liquids to provide better adhesion to the next layer. Around layer 4, a fourth layer 5 is disposed. Layer 5 is a thermally insulating layer comprising, for example, but not limited to, porous silica, SiO2, and/or polyacrylic acid, PAA, with an acoustic impedance lower than the previous optoacoustically active layer. Around layer 5, a fifth layer 6 is disposed. Layer 6 is a biocompatible and a biomolecular targeting layer, where biocompatibility is provided by polyethylene-glycol (PEG) and targeting is provided by one of more of antibodies or their active fragments, peptides, for example, RGD peptides, aptamers, and other specific targeting agents like folic acid or vectors, such as viruses.

Figure 2:
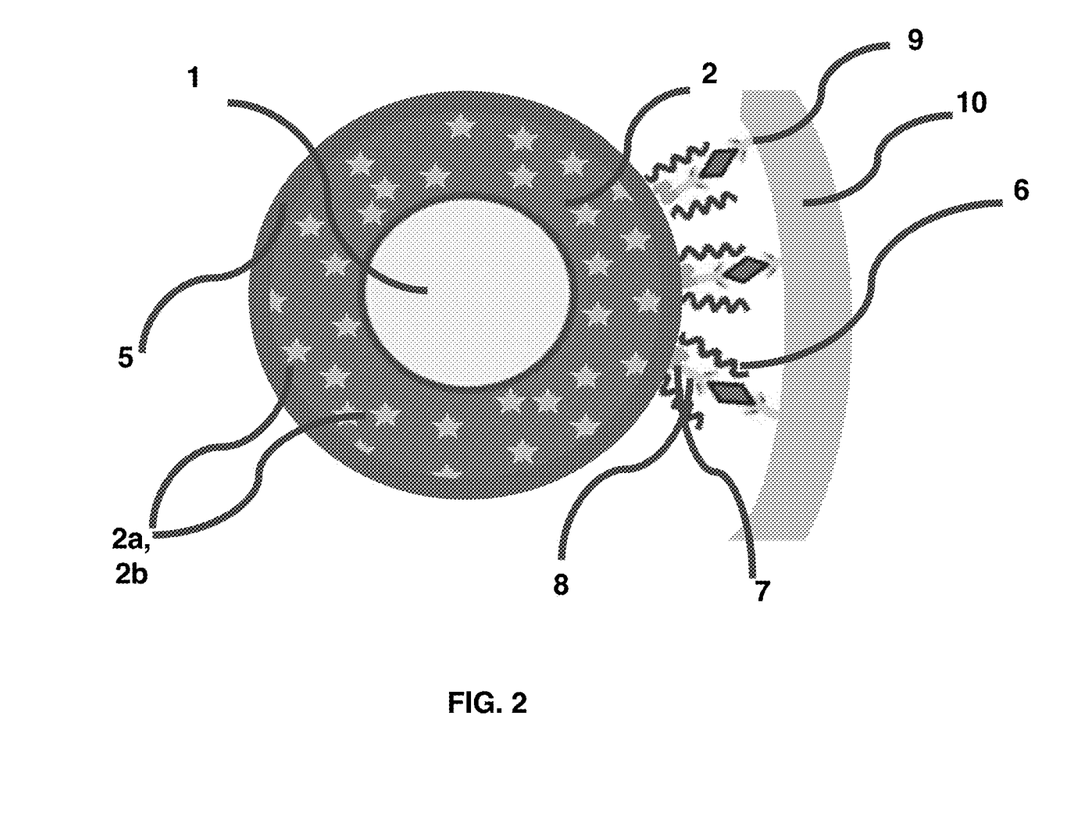
FIG. 2 depicts an example of a theranostic nanocomposite particle.

With continued reference to FIG. 1, FIG. 2 illustrates an optoacoustic-theranostic nanocomposite particle. The core 1 is a liquid having trong thermal expansion and a high thermo-acoustic efficiency, i.e., Gruneisen parameter. The core 1 also contains dissolved drugs or therapeutic agents. The optoacoustically active first layer 2 comprises at least one metal, for example, silver, gold or platinum, having at least one strong plasmon resonance peak in the near-infrared spectral range and/or a polymer, for example, copoly lactic acid/glycolic acid (PLGA) and/or protein, for example, albumin, and/or lipid, for example, phospholipids, triglycerides or sterols, and/or polysaccharide. For example, Chitosan, which is a linear polysaccharide composed of randomly distributed beta-(1-4)-linked D-glucosamine (deacetylated unit) and N-acetyl-D-glucosamine (acetylated unit) or galactose is a preferred polysaccharide. First layer 2 enables strong optical absorption by molecular or small nanoparticle based absorbers, represented by 2a,b which convert optical energy into heat and large values of thermo-acoustic efficiency. The fourth layer 5 is the thermally insulating layer. The fifth biocompatibility layer 6 comprises a long chain polyethylene glycol (PEG) and, optionally, is functionalized with a molecular linker 7 bound to targeting agents 8 such as monoclonal antibodies, peptides, aptamers, etc. The nanocomposite particle is attached to cancer-specific cell receptors 9 on the surface of the cell membrane 10. The second layer 3 and third layer 4 are not specifically highlighted in the figure.

Figure 3:
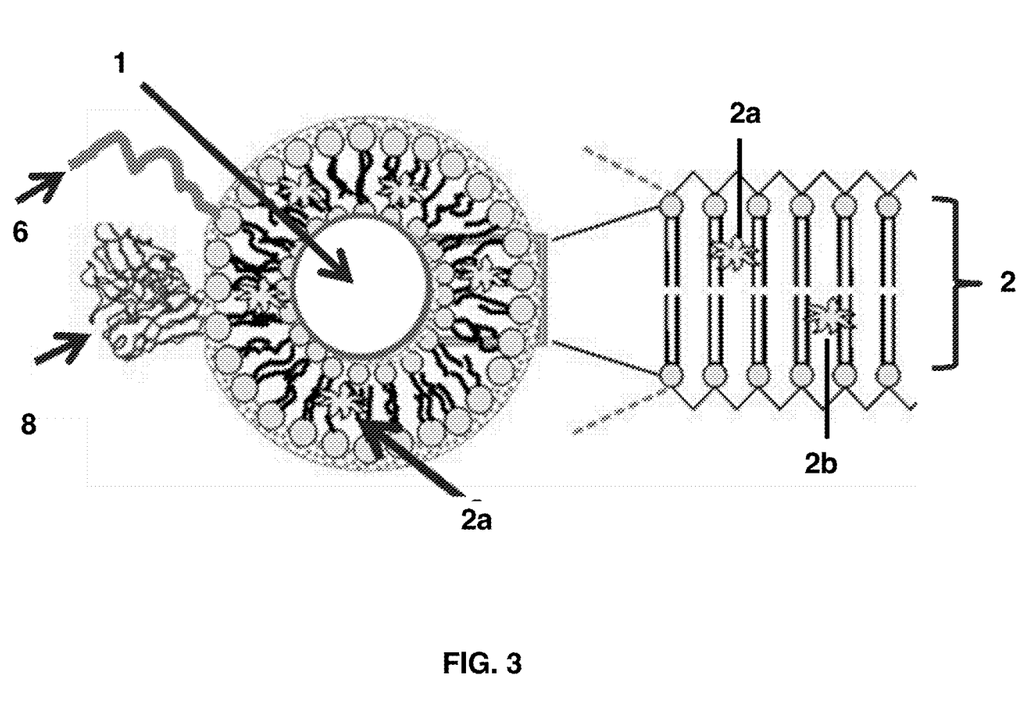
FIG. 3 depicts an example of another nanocomposite particle.

With continued reference to FIGS. 1 and 2, FIG. 3 illustrates the design of another optoacoustic-ultrasonic nanocomposite particle. The core 1 comprises a liquid with heavy gas, such as peflourocarbon, air or nitrogen. The first optoacoustically active layer 2 comprises a lipid bilayer with incorporated/intercalated optically absorbing inclusions represented by 2a. The inclusions comprise at least one of a metal nanoparticle having at least one strong plasmon resonance peak in the near-infrared spectral range and/or a dye and/or cabon nanoparticles and/or pigment, e.g., melanine, and/or this layer has the ability for strong optical absorption, conversion of optical energy into heat and large value of thermo-acoustic efficiency. The fifth biocompatibility layer 6 contains long chain polyethylene glycol (PEG) and optionally contains biomolecular targeting agents 8, such as antibodies, peptides, aptamers of nucleotides, and other targeting molecules such as folic acid, etc. The second layer 3, the third layer 4 and the fourth layer 5 are not specifically highlighted in the figure.

Figure 4A:
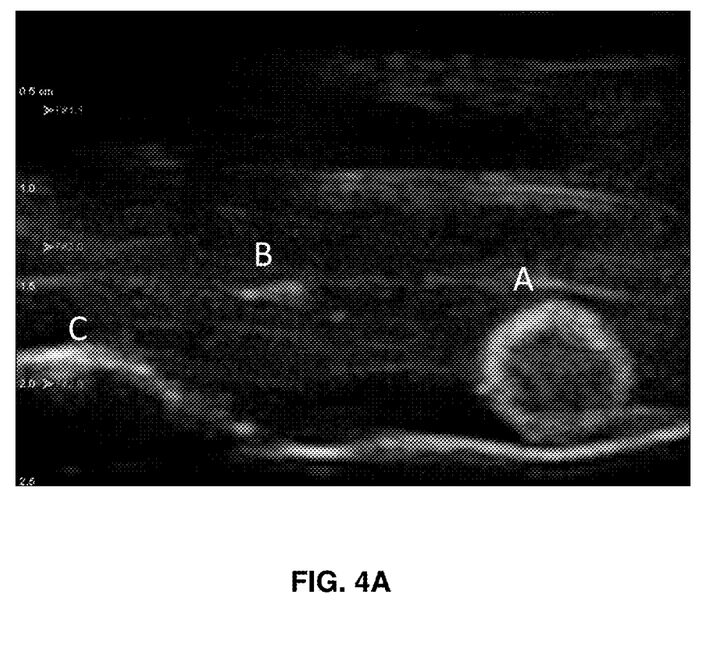
FIGS. 4A-4B depict ultrasonic contrast in a gelatin phantom before (FIG. 4A) and after (FIG. 4B) addition of nanocomposite particles.
Figure 4B:
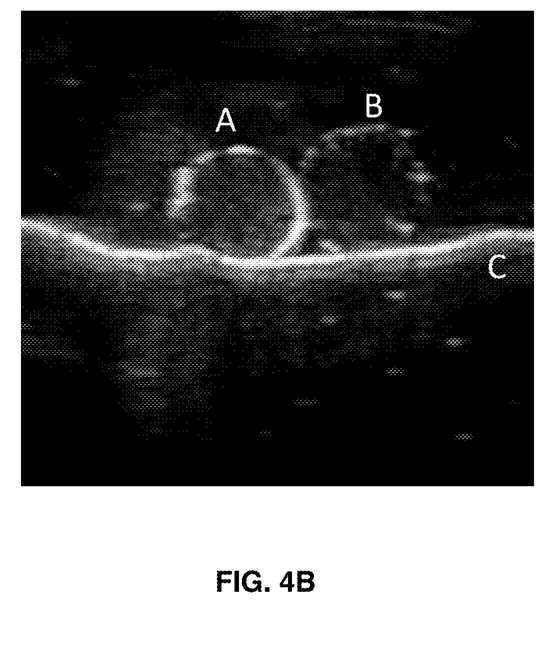

FIGS. 4A-4B are two images demonstrating significant improvement of the ultrasonic contrast of a 7 mm spherical gelatin phantom after addition of particles. A gelatin phantom with 1-50 μm glass microspheres is shown at A. A pure gelatin phantom is shown at B. A plastic membrane that separates the two acqeous compartments and that holds gelatin phantoms A and B in place. It is readily apparent that the addition of the particles resulted in enhanced contrast delineating the phantoms.

Figure 5A:
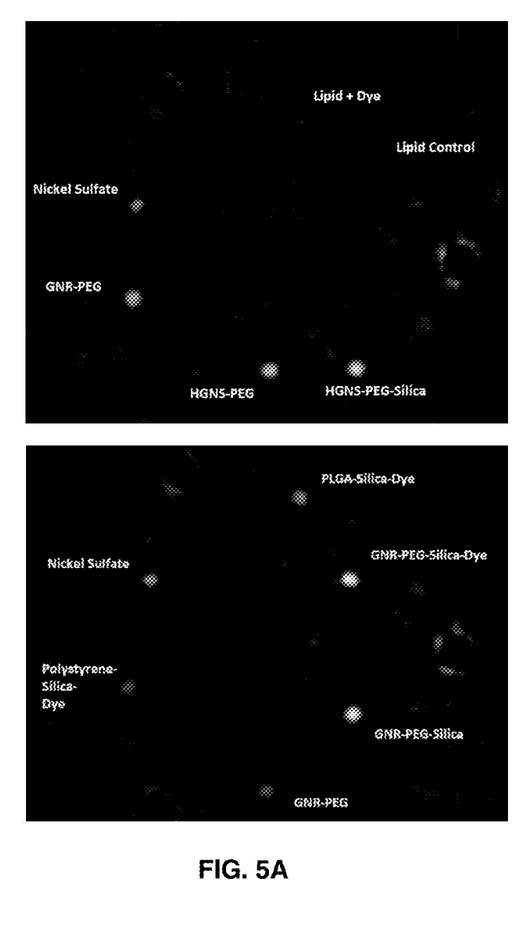
FIGS. 5A-5C depict optoacoustic images of thin plastic tubes in cross-section filled with different solutions (FIG. 5A) and optical absorption spectra of gold nanoshell solutions (FIG. 5B) and gold nanorod solutions (FIG. 5C).
Figure 5B:
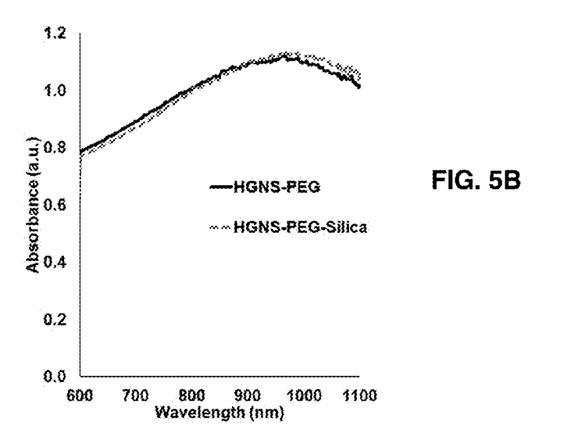
Figure 5C:
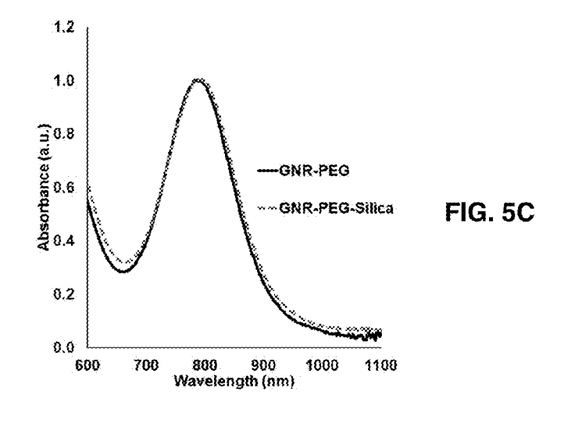

FIGS. 5A-5C are crossectional views of optoacoustic images of thin plastic tubes filled with different solutions. FIG. 5A shows the optical absorption spectra of some of the solutions, as identified. FIGS. 5B and 5C show that solutions of gold nanoshells and gold nanorods, respectively, had similar optical absorption at 800 nm which was the wavelength used to acquire the optoacoustic images. The solutions of gold nanorods (GNR-PEG) and hollow gold nanoshells (HGNS-PEG) that are covered with a biocompatible layer of polyethelene glycol show enhanced optoacoustic response due to optical absorption of the particles. The optoacoustic response visibly increases after those particles are additionally covered with an intermediate thermally insulating layer of silica (GNR-PEG-Silica and HGNS-PEG-Silica). The optoacoustic images also demonstrate that a significant optoacoustic response can be achieved from an optically absorbing dye embedded in a polymer matrix of a 0.5 μm microparticle coated with a thermally insulating layer of silica (PLGA-Silica-Dye).

Figure 6A:
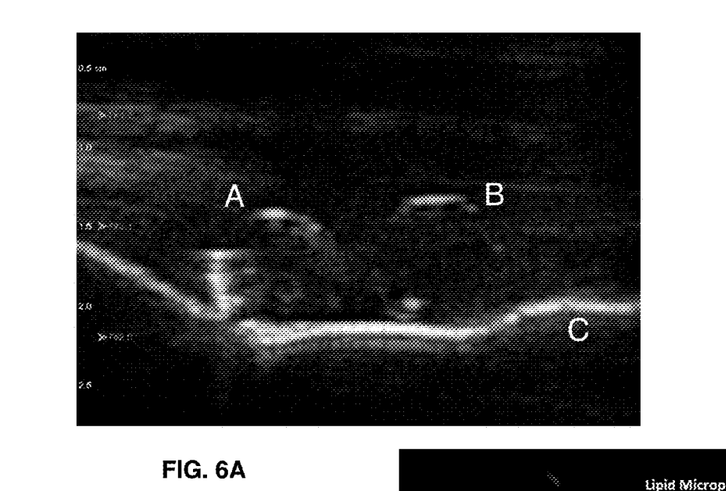
FIGS. 6A-6C depict acoustic (FIG. 6A), optical (FIG. 6B) and optoacoustric (FIG. 6C) contrast from lipid nanocomposite particles.
Figure 6B:
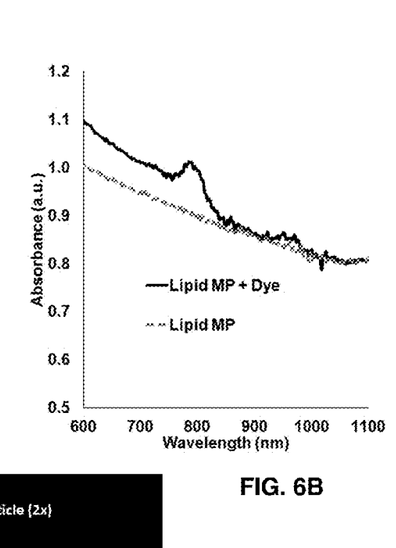
Figure 6C:
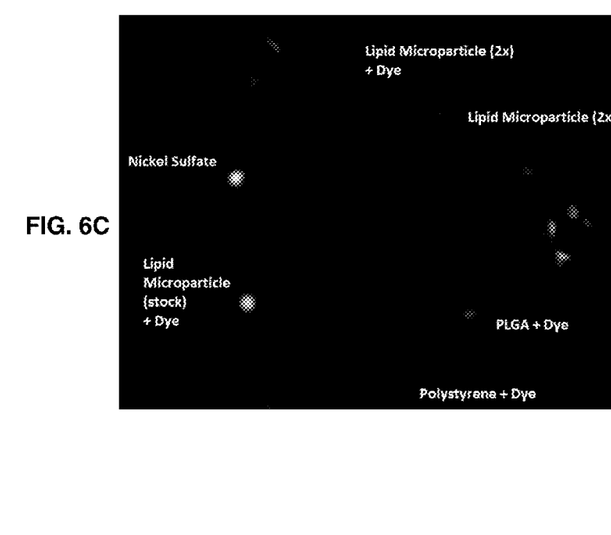

FIGS. 6A-6B Illustrate the acoustic, optical and optoacoustic contrast provided by lipid nanocomposite particles filled with an optically absorbing dye. In FIG. 6A, the ultrasonic image demonstrates improvement of the contrast of a 7 mm spherical gelatin phantom containing lipid microparticles. A gelatin phantom with lipid particles is shown at A. The pure gelatin phantom is shown at B. A plastic membrane separating the two aqueous compartments and holding the gelatin phantoms in place is shown at C. In FIG. 6B, the spectra shows an increase of optical absorption of the lipid particles at 800 nm after addition of the dye. FIG. 6C shows optoacoustic images of thin plastic tubes in cross-section that are filled with different solutions having similar optical absorption at 800 nm which is the wavelength used to acquire optoacoustic images. The solution of lipid microparticles comprising an optically absorbing dye (Lipid Microparticle (stock)+Dye) shows enhanced optoacoustic response due to optical absorption of the dye in combination with high thermoacoustic efficiency of lipids.

Figures 7A, 7B, 7C:
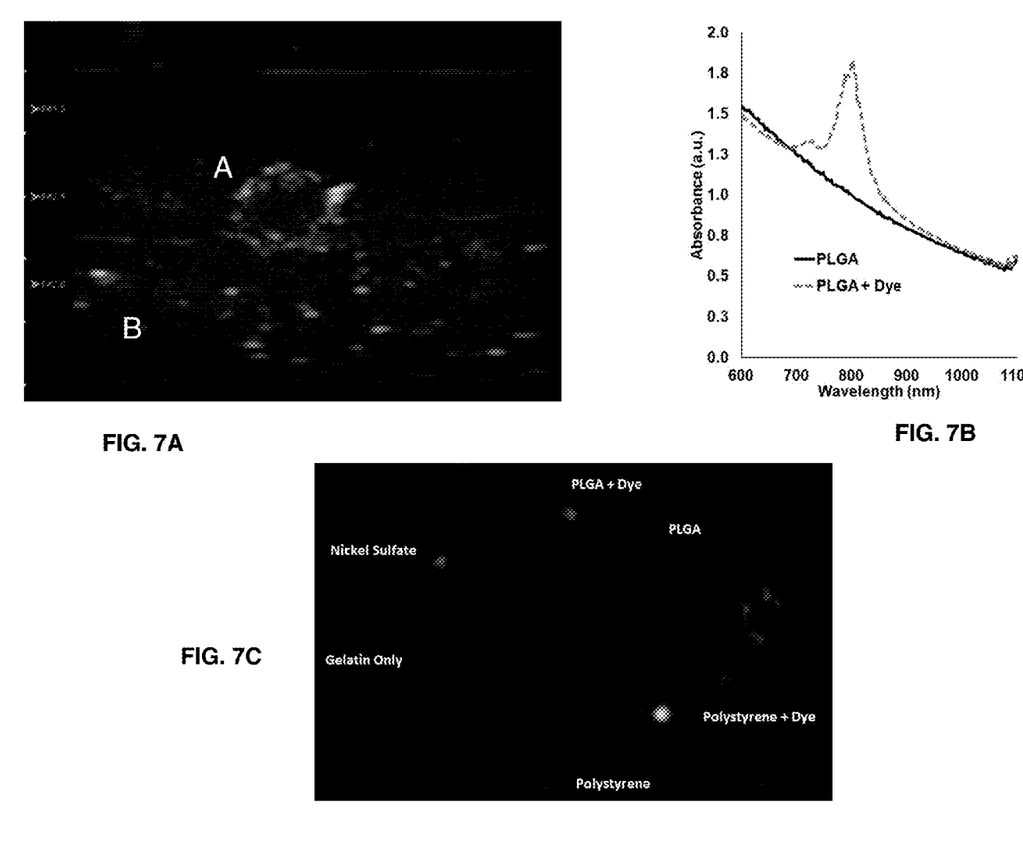
FIGS. 7A-7C depict ultrasonic (FIG. 7A), optical (FIG. 7B) and optoacoustic (FIG. 7C) contrast from polymer (PLGA) particles filled with an optically absorbing dye.

FIGS. 7A-7C Illustrate optoacoustic-ultrasonic contrast based on a solution of 0.5 μm polymer particles (PLGA) filled with optically absorbing dye. FIG. 7A is an image demonstrating ultrasonic contrast of a 7 mm spherical gelatin phantom containing dyed PLGA microparticles. The gelatin phantom with PLGA particles is shown at A. The gelatin base supporting the phantom is shown at B. FIG. 8B shows spectra demonstrating an increase of optical absorption of PLGA particles at 800 nm after the dye was embedded into polymer matrix. FIG. 7C shows optoacoustic images of thin plastic tubes in crossection that are filled with different solutions having similar optical absorption at 800 nm which is the wavelength used to acquire optoacoustic images. The solution of dyed PLGA microparticles (PLGA+Dye) show enhanced optoacoustic response due to optical absorption of the dye and thermoacoustic response of PLGA matrix. Having microparticles with a larger thermoacoustic response and/or lower thermal conductivity of the matrix can further increase optoacoustic efficiency as demonstrated by brighter optoacoustic images of the tube filled with a solution of polystyrene microparticles embedded with dye (Polystyrene+Dye).

Figure 8A:
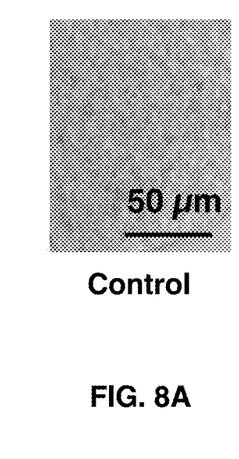
FIGS. 8A-8F depict the effectiveness of a PEG-HER2-mAB conjugated particle as a selective targeting agent.
Figure 8B:
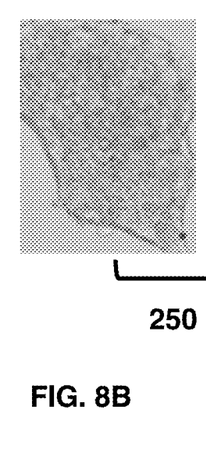
Figure 8C:
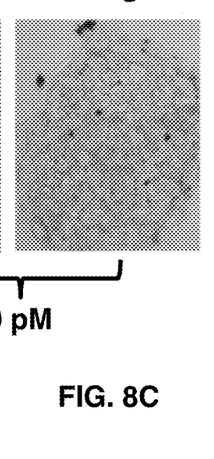
Figure 8D:
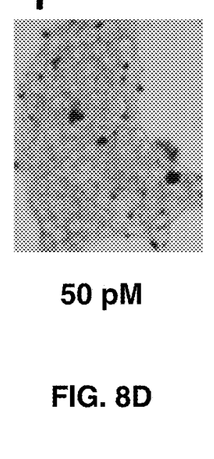
Figure 8E:
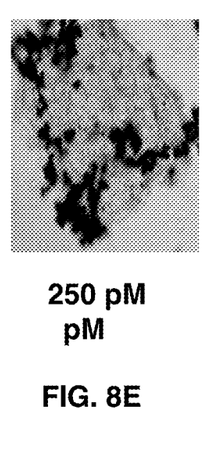
Figure 8F:
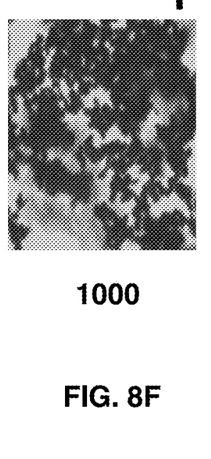

FIGS. 8A-8F demonstrates the biological effectiveness of a nanocomposite particle as a selective targeting agent. The outer most layer of the particle comprises poly(ethyleneglycol) for biocompatibility and Herceptin monoclonal antibody for affinity with HER2 receptors on the surface of BT-474 breast cancer cells. Optoacoustically active particles comprising gold nanorods conjugated with PEG and HER2-mAb effectively accumulated in BT-474 breast cancer cells as shown by silver staining method after 1-hour incubation time (magnification 20×). FIGS. 8A, 8B and 8C show intact cells, cells incubated with PEG-conjugated particles and cells conjugated with PEG+nonspecific IgG-conjugated particles, respectively. High selectivity of targeting particles is shown in FIGS. 8D, 8E and 8F in contrast to controls of cell incubated with particles conjugated only with PEG and particles conjugated with PEG plus nonspecific antibody immuno-gamma-globulin, IgG. Increasing concentration of particles resulted in increased accumulation in target breast cancer cells.

Figure 9A:
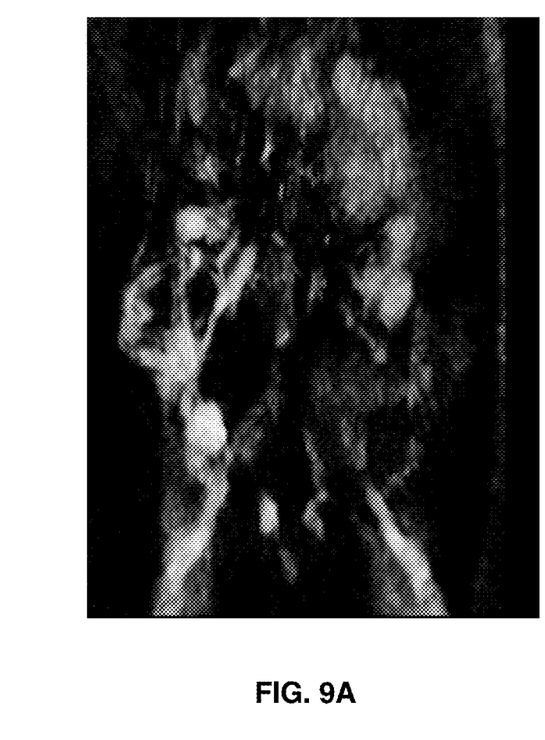
FIGS. 9A-9B are 2D projections of 3D optoacoustic images obtained in vivo of a breast tumor in a live mouse before (FIG. 9A) and after (FIG. 9B) of a PEG-Herceptin conjugated particle.
Figure 9B:
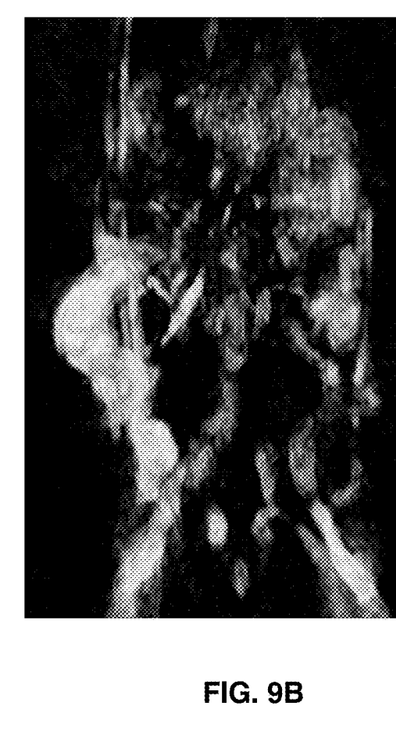

FIGS. 9A-9B are 2D projections of 3D optoacoustic images of a live mouse body bearing a human breast cancer tumor. Breast tumor receptors are clearly visualized using targeted optoacoustic contrast agent based on bioconjugated particles. FIG. 9A is a visualization of the mouse tumor based on its microvasculature before injection of the contrast agent. In FIG. 9B, after intravenous injection of nanocomposite contrast agent conjugated with PEG-Herceptin, distribution of targeted molecular receptors of HER2/neu in BT474 breast cancer cells became the dominating image feature with the highest contrast.

The following references are cited herein.
1. Oraevsky et al. U.S. Pat. No. 5,840,023.
2. Jaeger et al. IEEE Trans. Med. Imaging, 24(4): 436-440 (2005).
3. A. A. Oraevsky, Gold and silver nanoparticles as contrast agents for optoacoustic imaging, Chapter 30 in "Photoacoustic imaging and spectroscopy", ed. by L. Wang, Taylor and Francis Group, New York, 2009.

4. Kim et al. J. Biomed. Opt., 15(1), 010510 (2010).
5. Wang et al. J. Biomed. Opt. 17(4), 045001 (2012)
6. Wilson, K. H. and Emelianov, S. Proc. SPIE 7564, 75642P (2010).
7. Stride E. and Saffari N., Proc. Inst. Mech. Engrs 2003, Vol. 217 part H: J. Engineering in Medicine, P 429-446
8. Eghtedari et al. Nano Lett., 7(7), 1914-1918 (2007).
9. Kim et al. J. Control. Release, 146(2), 219-227 (2010).
10. Willmann et al. Radiology, 248(3), 936-944 (2008).
11. Bell, C. S. and Yu, S. U.S. Publication No. 2012/0258051
12. Begum et al. J Mater Sci, 45:3697-3706 (2010).

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A dual contrast agent designed to enhance optoacoustic-ultrasonic imaging, comprising:
    a nanocomposite particle having a core comprising a heavy gas or a liquid having a low energy threshold for transition into gas that can reflect and deflect ultrasonic waves, effective to enhance response to incident transient ultrasonic pressure waves and five layers disposed around the core, said five layers comprising:
    a first layer comprising an expandable and contractible polymer, protein, lipid or polysacharide disposed in a mechanically confining relationship to the core;
    a second layer of an optoacoustically active medium comprising a matrix of biodegradable substances having a significant thermal expansion coefficient and strong thermo-acoustic efficiency, said matrix comprising one or more of inclusions or embedded molecules or nanoparticles with a strong optical absorption peak in at least one predetermined wavelength or wavelength range, said inclusions effective to rapidly and effectively nonradiatively convert optical energy into heating of the matrix;
    a third thin bonding layer comprising one or more silica compounds as an adhesive between adjacent layers;
    a fourth thermally insulating layer comprising one or more compounds wherein the fourth layer has an acoustic impedance lower than the second optoacoustically active layer; and
        a fifth biocompatibility and biomolecular targeting layer comprising a biocompatible polyethylene-glycol (PEG) and one or more targeting agents or vectors.

2. The dual contrast agent of claim 1, wherein the nanocomposite particle comprises at least two layers, the contrast agent further comprising a thin bonding layer disposed between said adjacent layers.

3. The dual contrast agent of claim 2, wherein the bonding layer comprises a linking molecule, a linking substance or a linking medium.

4. The dual contrast agent of claim 1, wherein the core comprises a gas, liquid or emulsion having ultrasound generating properties upon interaction with incident optical energy and ultrasound reflecting properties upon interaction with incident ultrasound energy.

5. The dual contrast agent of claim 4, wherein the gas is air, a perfluorocarbon gas or nitrogen or other heavy gas.

6. The dual contrast agent of claim 4, wherein the liquid or emulsion is expandable upon heating or convertible to a gas.

7. The dual contrast agent of claim 1, wherein each of said layers comprises separately or in combination smaller layer portions, sublayers or subcomponents.

8. The dual contrast agent of claim 1, wherein the first layer compound comprises one or more of a metal having plasmonic resonance at a predetermined range of wavelengths, a polymer, a protein, a sugar, or a lipid each with embedded or intercalated absorbing molecules or small nanoparticles.

9. The dual contrast agent of claim 8, wherein said metal is gold, silver or platinum, said polymer is poly(lactic-co-glycolic acid) (PLGA), said protein is albumin, and said sugar is chitosan or galactose.

10. The dual contrast agent of claim 1, wherein the second layer compound an ultra-high-molecular-weight polyethylene, polyvinylidene fluoride, polytetrafluoroethylene, high impact polystyrene, or nylon-6.

11. The dual contrast agent of claim 1, wherein the third layer silica compound is tetraethyl orthosilicate, 3-aminopropyl-triethoxysilane, 3-(trimethoxysilyl)propyl methacrylate, ethyl silicate, sodium silicate or other bonding liquids.

12. The dual contrast agent of claim 1, wherein the one or more compounds comprising the fourth layer are porous silica, silicon dioxide, or polyacrylic acid (PAA).

13. The dual contrast agent of claim 1, wherein the targeting agent or vector is antibodies or active fragments thereof, RGD peptides or other peptides, aptamers, folic acid or viruses.

14. A method for enhancing contrast in a tissue volume of interest in a subject during optoacoustic-ultrasonic imaging, comprising the steps of:
    contacting the tissue volume of interest with the dual contrast agent of claim 1;
    delivering incident optical energy to the tissue volume of interest and to the dual contrast agent; and
    delivering ultrasonic energy to the tissue volume of interest and to the dual contrast agent;
    wherein the nanocomposite particle comprising the dual contrast agent generates and emits detectable ultrasonic pressure waves upon interaction with the incident optical energy in addition to ultrasonic pressure waves generated and emitted by the tissue volume and reflects the incident ultrasonic energy upon interaction therewith in addition to incident ultrasonic energy reflected by the tissue volume, said addition of the detectable ultrasonic pressure waves and reflected ultrasonic energy from the dual contrast agent thereby enhancing contrast in the tissue volume during optoacoustic-ultrasonic imaging.

15. An optoacoustic-ultrasound imaging method with enhanced contrast, comprising the steps of:
    targeting a plurality of nanocomposite particles to the tissue volume of interest in a subject, wherein said nanocomposite particles comprise:
        a core comprising a fluid having ultrasound generating properties at a predetermined range of electromagnetic wavelengths;

a first layer disposed around the core comprising one or more optical energy absorbing compounds effective to convert absorbed optical energy into heat and thermally expand;

a second layer disposed around the first layer comprising a thermally insulating compound with an acoustic impedance lower than the first layer or matching that of biological tissue or a combination thereof; and a third layer disposed around the second layer comprising a nanocomposite particle bioprotective compound or a targeting vector or a combination thereof;

delivering optical energy and ultrasound energy to the tissue volume and nanocomposite particles;

detecting ultrasonic pressure waves generated by the tissue and by the nanocomposite particles upon interaction with the optical energy;

detecting ultrasonic energy reflected by the tissue and by the nanocomposite particles upon interaction therewith; and producing an optoacoustic-ultrasound image based on a combination of the detected ultrasonic pressure waves and on a combination of the reflected ultrasonic energy from the tissue and nanocomposite particle, wherein the combination provides an image with enhanced contrast.

16. The optoacoustic-ultrasound imaging method of claim 15, wherein the nanocomposite further comprises a bonding layer or linker disposed between adjacent layers.

17. The optoacoustic-ultrasound imaging method of claim 16, wherein the bonding layer or linker comprises a linking molecule, a linking substance or a linking medium.

18. The optoacoustic-ultrasound imaging method of claim 15, wherein the core fluid is air, perfluorocarbon gas or nitrogen or other heavy gas or is a liquid or emulsion that is expandable upon heating or convertible to a gas.

19. The optoacoustic-ultrasound imaging method of claim 15, wherein each of said layers comprises separately or in combination smaller layer portions, sublayers or subcomponents.

20. The optoacoustic-ultrasound imaging method of claim 15, wherein the first layer compound comprises one or more of a metal having plasmonic resonance at a predetermined range of wavelengths, a polymer, a protein, a sugar, or a lipid each with embedded or intercalated absorbing molecules or small nanoparticles.

21. The optoacoustic-ultrasound imaging method of claim 20, wherein said metal is gold, silver or platinum, said polymer is poly(lactic-co-glycolic acid) (PLGA), said protein is albumin, and said sugar is galactose.

22. The optoacoustic-ultrasound imaging method of claim 15, wherein the second layer compound is silica oxide.

23. The optoacoustic-ultrasound imaging method of claim 15, wherein the second layer compound is a polymer.

24. The optoacoustic-ultrasound imaging method of claim 15, wherein the third layer polymer is polyethylene glyol (PEG) and the targeting vector is one or more of a peptide, an antibody, an aptamer, a nucleotide, or a virus.

* * * * *